United States Patent [19]

Tower

[11] Patent Number: 5,002,559
[45] Date of Patent: Mar. 26, 1991

[54] PTCA CATHETER

[75] Inventor: Allen J. Tower, Hopkinton, N.Y.

[73] Assignee: NuMed, Hopkinton, N.Y.

[21] Appl. No.: 443,387

[22] Filed: Nov. 30, 1989

[51] Int. Cl.$^5$ ............................................. A61M 29/00
[52] U.S. Cl. ..................................... 606/194; 604/96;
128/772
[58] Field of Search ................. 604/164, 96; 606/194;
128/772

[56] References Cited

U.S. PATENT DOCUMENTS 4,886,067  3/1989  Palermo et al. ...................... 128/657

OTHER PUBLICATIONS

Improved Method for Transcatheter Retrieval of Intracoronary Detached Angioplasty Guidewire Segments, Serota et al., Catherization and Cardiovascular Diagnosis 17:248–251, (1989).

Primary Examiner—Vincent Millin
Assistant Examiner—Jennifer L. Doyle
Attorney, Agent, or Firm—Wall and Roehrig

[57] ABSTRACT

A PTCA catheter is provided in which the extreme distal end is reduced to a diameter of 3 thousandths of an inch and enclosed in a coiled spring which is welded to the guidewire of the catheter at its tip and at a thicker 8 thousandths diameter portion of the guidewire to increase the strength of the tip and reduce breakage when inserted in a coronary artery. A dual lumen catheter body is provided at the proximal end for capturing and actuating the guidewire and for inflating the balloon at the distal end.

15 Claims, 4 Drawing Sheets

PTCA CATHETER

BACKGROUND OF THE INVENTION

This invention relates to PTCA Balloon Catheters and in particular to a catheter, and process for making same, to minimize breakage of the tip of the guidewire.

Percutaneous transluminal coronary angioplasty (PTCA) balloons and guidewires have been used for sometime now in the alleviation of stenosis of coronary arteries rather than open heart surgery for many situations. While highly effective in proper applications the procedure has an infrequent but potentially serious complication from breakage and retention in the coronary vascular tree of the tip of the angioplasty balloon guidewire. The seriousness of this problem can be better appreciated by a review of the article "Improved Method for Transcatheter Retrieval of Intracoronary Detached Angioplasty Guidewire Segments" in volume 17:248-251 (1989) of the Catheterization Cardiovascular Diagnosis Journal.

In order to be able to maneuver the angioplasty balloons to appropriate locations in the coronary vascular tree, the tip of the guidewire must be very small in diameter and highly flexible, so it can be properly maneuvered by the attending physician. This has resulted in the use of very finely drawn wires where the tip of the guidewire is reduced to a few thousandths of an inch in diameter, typically three, which permits easy bending and guiding through the artery system. It also however, becomes a weak link in the equipment which occasionally can be damaged or broken leaving a small piece of guidewire in the artery of the patient. Since the long term effects of leaving such a foreign object in the artery is unknown, many doctors prefer to perform the retrieval procedures that are described in detail in the above referenced article rather than take the risk. This subjects the patient to additional trauma which can be eliminated by use of the apparatus of the present invention.

SUMMARY OF THE INVENTION

It is therefore an object of the present invention to improve PTCA balloon catheters. It is another object of the present invention to provide a PTCA balloon catheter and guidewire that is significantly strengthened against breakage while retaining or increasing flexibility and guideability. It is another object of the present invention to provide a PTCA balloon and guidewire construction in which the tip of the guidewire is enclosed in a highly flexible coiled spring member which is welded to the guidewire at a substantially larger diameter portion of the guidewire than the very smallest diameter tip portion. It is another object of the invention to provide a method for protecting the tip of a guidewire in a PTCA balloon catheter from breaking at the extreme distal end thereof. It is another object of the present invention to provide a PTCA balloon catheter in which the guidewire tip can be twisted without twisting the catheter balloon. It is another object of the present invention to provide for greater patient safety during PTCA procedures involving the use of guidewires of extremely small diameter.

These and other and further objects of the present invention are attained by means of a PTCA balloon catheter and guidewire positioned in a elongated cylindrical catheter body and having a progressively tapered distal end of the guidewire enclosed in a spiral wound platinum spring. The spring is welded to the guidewire at its distal and proximal ends. The assembled guidewire and spring are enclosed in a plastic sheath from the proximal end of the spring to the distal end of the balloon. The sheath is sealed to the guidewire at the proximal end of the spring. The tubular balloon is disposed about the distal end of the catheter body and the spring member to a point approximately at the middle thereof to seal the balloon about the lumen for inflating the balloon, when the device is positioned in the appropriate artery.

BRIEF DESCRIPTION OF THE DRAWINGS

For a better understanding of these and other objects of the present invention, reference is made to the following detailed description of the invention, which is to be read in association with the accompanying drawings wherein.

Figure 1:
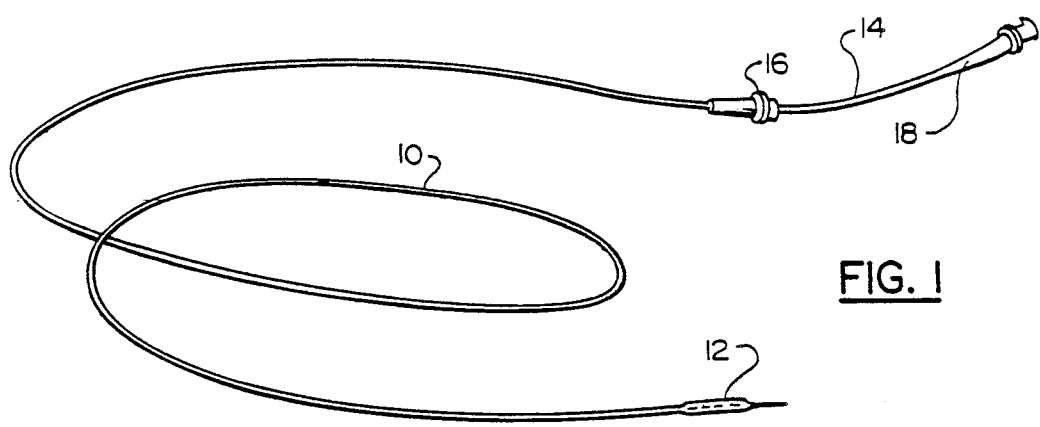
FIG. 1 is a perspective view of a PTCA balloon and guidewire according to the present invention.

Referring now to the drawings and particularly FIG. 1 there is shown the PTCA balloon catheter 10 according to the present invention. The catheter 10 consists of the balloon and guidewire tip portion 12, and the manipulating or control end 14. Control end 14 generally consists of twisting ferrule 16 and a connector fitting 18 for attaching a hypodermic syringe or other "pump" for inflating the balloon at the distal end of the catheter.

Figure 2:
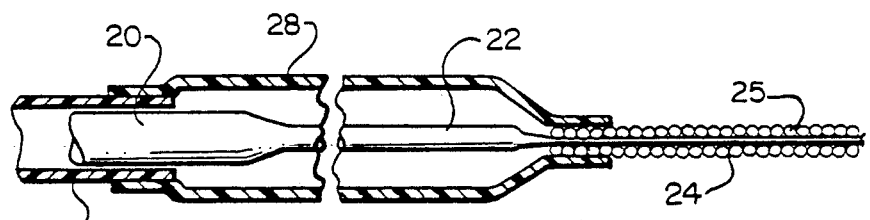
FIGS. 2 and 2a are cross-sectional views, partially broken away, of the guidewire tip of PTCA balloon catheters in accordance with the prior art.

In FIG. 2 there is shown a cross-sectional view of the tip of the guidewire and balloon according to the prior art as known by applicant. In this configuration the guidewire 20 is reduced from a diameter on the order of 14 to 16 thousandths to a diameter of 8 thousandths at 22 and then further reduced down to a diameter of approximately 3 thousandths (0.003") at 24. A coiled spring 25 is disposed about the tip of the guidewire and fixed thereto to form a unitary tip. The catheter balloon 28 is secured, at its proximal end to the catheter body 30, and at its distal end, to the proximal end of spring 25. The guidewire 20 is a smaller diameter than the interior diameter of the catheter body 30 and the catheter body 30 serves as the lumen for directing inflating air to the balloon member. In this configuration twisting of the guidewire twists the balloon 28 also, which under certain circumstances is very undesirable.

Figure 2A:
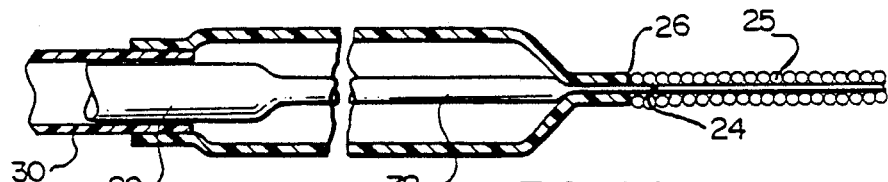

FIG. 2a shows another prior art device in which the spring 25 is welded to the tip of guidewire 20 and balloon 28 is secured to the catheter 30 at the proximal end and to guidewire 20 at its distal end approximately 1 mm proximally of the proximal end of the spring 25.

In use this prior art device has tended to break at the 3 thousandths diameter portion at 26 leaving a piece of plastic and/or stainless steel wire in the artery of the patient. This has been a cause for concern and while infrequent it is a very serious problem with the prior art device.

Figure 3:
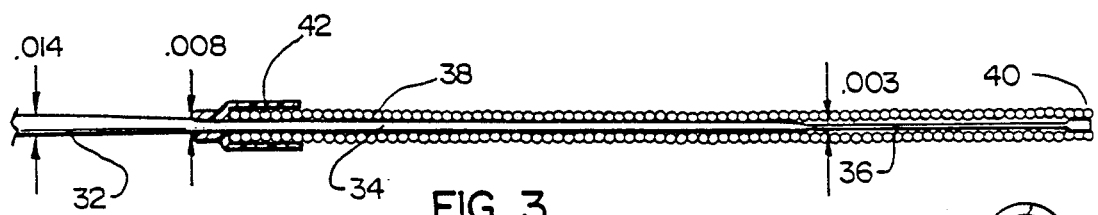
FIG. 3 is a cross-sectional view on an enlarged scale of the tip of the guidewire according to the present invention prior to covering with a plastic sheath.
Figure 3A:

Referring now to FIG. 3 there is shown a guidewire tip according to the present invention. In this configuration the guidewire 32 has a basic diameter of 14 to 16 thousandths and tapers down to a diameter of 8 thousandths at 34 and then tapers again to a diameter of approximately 3 thousandths at 36 which extends for the last two centimeters of the tip. The tip of the guidewire 32 has disposed about it a coiled, very flexible spring 38 made of radiopaque platinum. Spring 38 is hollow and is slipped over the tip of the wire 32 until the end of the 3 thousandths section 36 is even with the end of the spring 38. The spring 38 is then welded to the guidewire 32 at the extreme tip 40 and at the proximal end of spring 42, which is on the 8 thousandths section 34. This allows the mid protion of the guidewire to "float" within the spring 42. The fine wire portion 36 (prior to insertion in the spring), is flattened to approximately a 6 thousandths width by a thickness something on the order of five-ten thousandths of an inch (0.0005").

Figure 4:
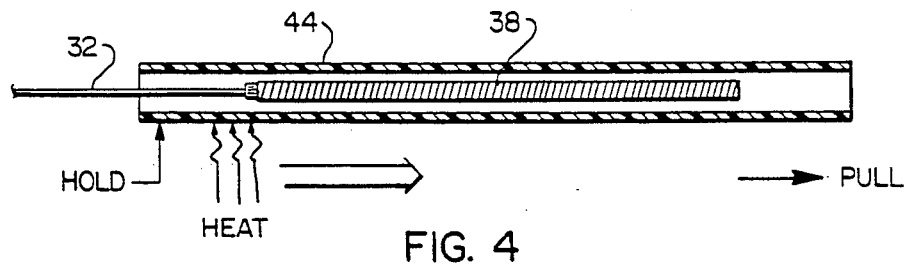
FIG. 4 shows the method of applying a plastic sheath over the spring member.

As shown in FIG. 4 after the spring is welded to the guidewire 32 as shown in FIG. 3 a plastic sleeve 44 is fed over top of the welded spring past the proximal end and about the guidewire 32. The proximal end is held and the sleeve 44 is heated and stretched from adjacent the proximal end of the spring 38 to the distal end. This causes the sleeve to heat shrink about the spring 38 and to form a tight seal about the guidewire 32. The proximal end of the sleeve is also adhesively secured to the wire 32 by an epoxy adhesive applied to the junction of the proximal end of the sleeve 44 and the wire 32. This forms a substantially airtight joint about the wire 32 and the excess length of the sleeve 44 is cut off to approximately 2 millimeters from the proximal end of the spring.

Figure 6:
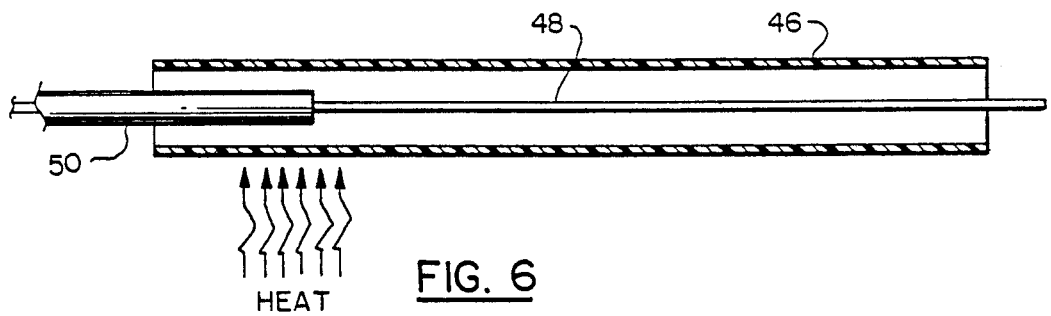
FIG. 6 is a view similar to FIG. 4 showing the method of securing the tubular balloon to the catheter body.
Figure 7:
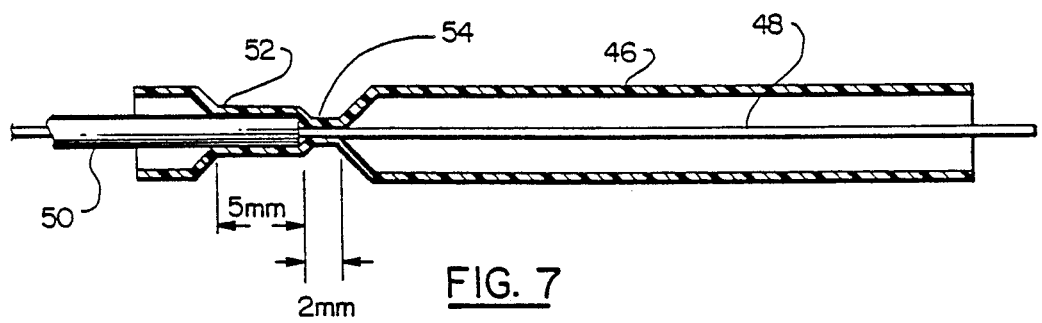
FIG. 7 is a further detail of the method of applying the balloon to the catheter body.
Figure 8:
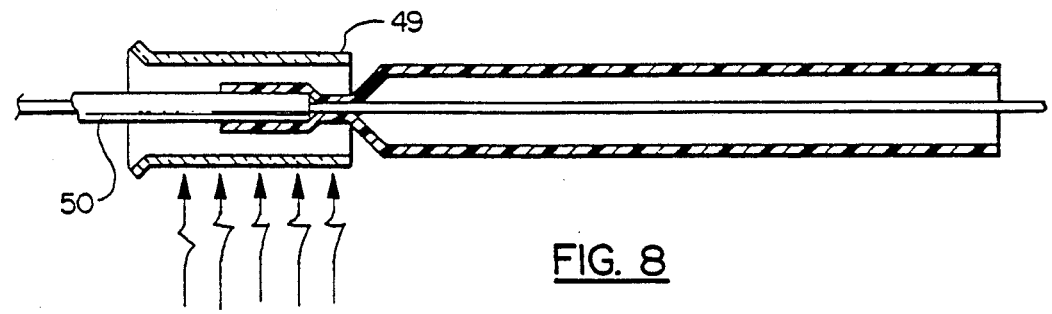
FIG. 8 is a still further step in the method of applying the balloon to the catheter body.

The next step in the forming of the PTCA catheter is to insert a dummy wire 48 of twenty thousandths (0.020") diameter through the catheter body so as to extend out the end thereof some distance as shown in FIG. 6. A tubular thin wall balloon 46 is then inserted over the dummy wire 48 and over the distal end of the catheter body 50 as may be seen in FIG. 6,7,8. The balloon sleeve 46 is heated at the proximal end as shown in FIG. 6 and 7, to form a tight seal about the catheter body 50 over a length of approximately 5 millimeters and for a distance of about 2 millimeters from the distal end of the catheter body along the dummy wire 48 forming a neck portion 54, all as shown in FIG. 7 and 8. A glass sleeve 49 is placed over the seal, heated and molded until completely bonded. During the manufacturing of the catheter and particularly the heating of the ends of the balloon 46, the balloon body portion itself may be covered with a dampened cloth to prevent damage thereto.

Figure 5:
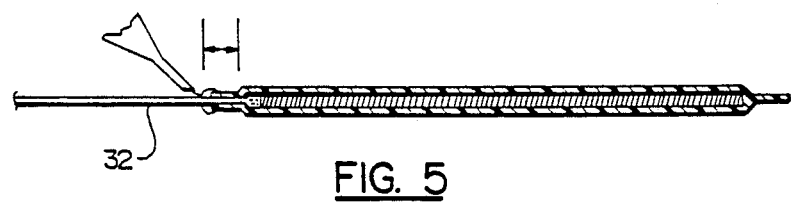
FIG. 5 is a further detail of the sealing of the plastic sheath over the spring member.

After the neck portion 54 is formed about the dummy wire 48 the wire 48 is removed from the catheter body 50 as shown in FIG. 8. After the wire 48 is withdrawn, the guidewire assembly 32 of FIG. 4 and 5, is inserted through the distal end of the catheter body 50 until it is adjacent to the neck portion 54 of the balloon 46. Care is taken to make sure that the sealed and welded end 42 of the spring 38 is not inserted in the necked down portion 54, but is spaced distally therefrom. This configuration, is shown clearly in FIG. 9 and 10.

Figure 10:
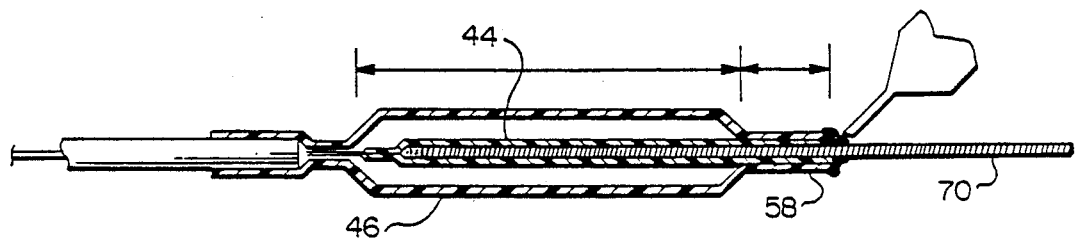
FIG. 10 is a view of the completed construction of the guidewire tip after positioning in the catheter body.
Figure 11:
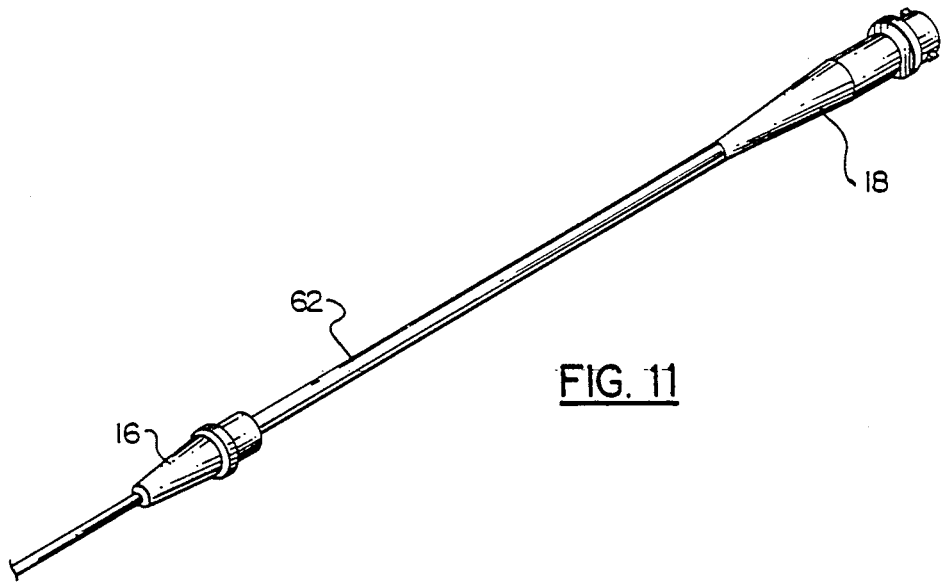
FIG. 11 is a perspective view of the proximal end of the catheter according to the present invention.

The next step in the manufacture of the catheter according to the present invention, is to heat the balloon at 58 approximately 2 centimeters from the proximal neck end 54, until it heat shrinks onto the sleeve 44 at the area 58. This makes a tight bond between the balloon 46, and the sleeve 44, at the distal end of the balloon. As shown in FIG. 5, epoxy is also applied to this joint which will wick between the sleeve and the balloon to further seal the joint thereabout, as can be seen in FIG. 10. The sleeve 44 and the balloon 46 are trimmed away from the spring portion extending distally out of the assembly, so that approximately 2 centimeters of exposed spring is left extending outwardly distally from the distal end of the balloon 46.

Figure 9:
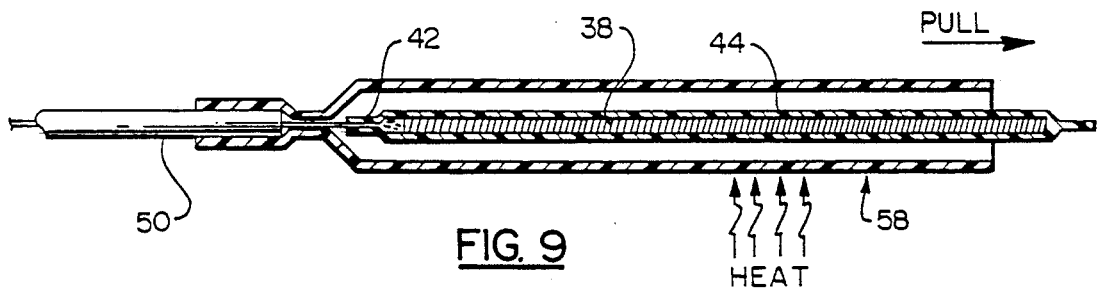
FIG. 9 shows the completed left-hand portion of the securing of the balloon to the catheter body, the insertion of the guidewire therein, and indicates the method of securing the right-hand end to the spring sleeve.
Figure 12:
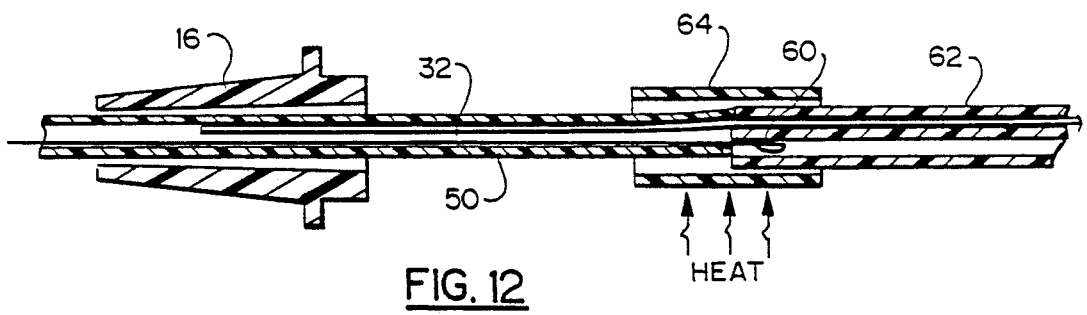
FIG. 12 is a cross-sectional view of the end shown in FIG. 11 with the ferrule displaced from the double lumen portion.
Figure 13:
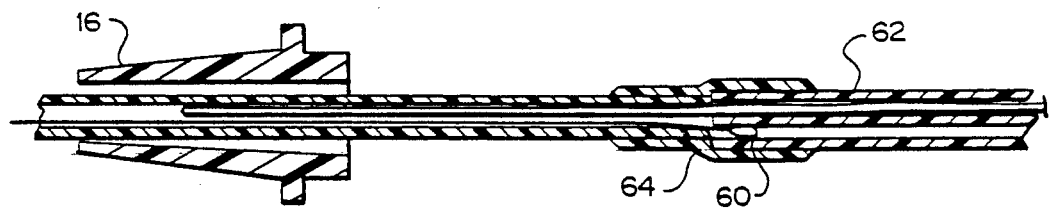
FIG. 13 is a view similar to FIG. 12 showing another step in the process of joining the dual lumen catheter to the single lumen catheter portion of the subject invention.
Figure 14:
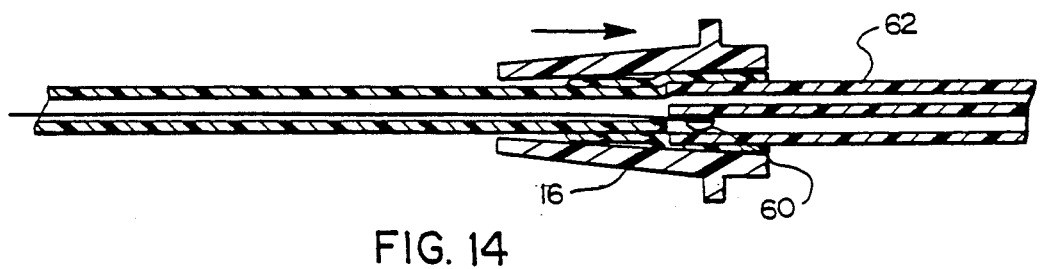
FIG. 14 is a view of the completed joint of the dual lumen and single lumen catheter body portions.

When the guidewire 32 with the spring assembly 38 attached thereto was inserted into the catheter body 50 in FIG. 9 and 10, as described above it was extended through the distal end of the catheter body 50 until it projected out of the proximal end. The next step in the manufacture of this PTCA catheter is to fasten a manipulating and inflating lumen portion to the proximal end of the catheter body 50. As may be seen in FIGS. 12-14, the guidewire 32 extends outwardly of the body 50 and is folded back on its self to form a loop 60. A ferrule 16 is positioned over the body 50 for future use. A dual lumen member 62 is then butted against the catheter body 50, so that the loop 60 of the wire 32 is positioned within one of the lumens of the dual lumen body portion 62, where it is captured and securely engaged. A sleeve 64, is positioned over the junction of the lumens and the entire assembly heated to shrink it about the juncture of the two lumen body 62 and the single lumen catheter body 50 to form a plastic welded joint in which the looped end of the wire 32 is captured in the one lumen of the body portion 62 and the other lumen is positioned in fluid communication with the interior of the body 50. This permits air to be pumped through catheter body 50 to inflate the balloon 46 by using a hypodermic syringe or other pump mechanism inserted in the connector 18, which is now in communication with the interior of body 32 and the balloon 46. The balloon thus can be inserted in an artery to the desired location of the stenosis or other problem and inflated as desired.

In operation the catheter is steered through the desired artery by rotating or twisting the exposed tip 70 of the spring 38. As may be seen in FIG. 10, the tip 70 extends approximately 2 centimeters beyond the balloon and can be twisted and deflected readily because of the friction of the balloon in the artery and the very thin 3 thousandths of an inch diameter (0.003") flattened end of wire 32, which is positioned within the spring and welded thereto at the extreme distal end. The spring tip has an internal diameter of approximately 8 thousandths of an inch (0.008") as described above and the exterior is on the order of 12 to 14 thousandths of an inch (0.012" to 0.014".) Because of the coil construction of the spring 38, a very flexible tip portion 70 is obtained which can be readily bent to lead the catheter into the desired branch of the vascular tree for proper positioning of the balloon in the stenosis area.

Twisting of the ferrule 16 will cause the wire 32 to be twisted because the loop 60 is captured by one lumen of body 62 and secured by ferrule 16, as described above. The twisting of the wire 32 will be transmitted down the length of the wire to its distal end where at both the proximal end and distal end of spring 70, the wire is secured to the spring. The spring will tend to twist, particularly at the free end 70, but also at the proximal end. The catheter body 50 also will twist with the ferrule 16, adjacent to the ferrule 16 but because of it long length and flexible nature, the distal end of the body 50 will tend to remain stationary. The balloon portion 46, when in the coronary artery will tend not to rotate due to the friction with the artery itself. The spring 38 being twisted at both ends thereof, by the wire 32 where it is welded to the spring, will tend to twist the balloon distal end but because the spring is of a helical construction, the spring itself will tend to absorb some of this twisting, sleeve 44 will absorb some, and also the spring itself will slip within sheath 44 at the distal end of balloon 46, so that the twisting will not be transmitted directly to the balloon 46, at the end 58 where the balloon is sealed to the sleeve 44, of the spring 38. Thus, while the spring tip 70 will twist the balloon end 58 will be held essentially stationary. It has been found that in actual operation the ferrule 16, can be given several turns without significantly twisting the balloon portion 46.

The spring 38 being welded to the wire 32 at the 8 thousandths (0.008") diameter area 42 and being helicly wound, has much greater flexibility than the 3 thousandths diameter wire end. Even though the spring wire itself has a diameter of only 2-3 thousandths of an inch (0.002"-0.003"), the composite strength of the wound spring is significantly greater, resulting in a composite strength several orders of magnitude greater than the single wire tip of the prior art configuration of FIG. 2. Also the flexibility of the tip 70, is equal to or superior to the flexibility of the distal tip of the guidewire of the prior art devices of FIG. 2 and twisting of the balloon 46 is essentially eliminated.

Thus, the safety and security of the system is greatly enhanced, and there is provided an extremely flexible, easily steered tip for guiding the catheter into the particular branch of the coronary vascular tree.

While this invention has been explained with reference to the structure disclosed herein it is not confined to the details set forth on this application and is intended to cover any modifications and changes which may come within the scope of the following claims.

What is claimed is:

1. A PTCA catheter that includes an elongated, hollow catheter body having a distal end and a proximal end;
    a guidewire with a main diameter smaller than the internal diameter of said body;
    said guidewire being positioned in said catheter body and having its distal end tapering in multiple steps from said main diameter to a very small diameter flexible tip;
    said tip portion extending outwardly of said catheter body for at least two tapered steps;
    a flexible coiled spring positioned about said guidewire tip and extending over at least two tapered guidewire steps;
    at least one end of said coiled spring being welded to said guidewire;
    a plastic sheath secured about said spring and the adjacent portion of said guidewire at the proximal end of said spring;
    a thin walled balloon secured at one end about the distal end of said catheter body and at the other end about said plastic sheath covering said spring; and
    control means operatively connected to said guidewire at the proximal end thereof for causing the distal tip of said coiled spring to twist and bend to steer the PTCA catheter to the desired artery, and for inflating said balloon.

2. A device as described in claim 1 wherein said guidewire tapers at its distal end in two steps from the main diameter to the tip diameter.

3. A device as described in claim 2 wherein said main diameter of the guidewire is in the range of 14-16 thousandths of an inch and tapers to 8 thousandths of an inch in diameter and then to 3 thousandths of an inch diameter at the distal tip.

4. A device as described in claim 3 wherein said distal 3 thousandths of an inch diameter tip of the guidewire is flattened at its tip to a width of approximately 6 thousandths by 5/ten thousandths of an inch thickness.

5. A device as described in claim 4 wherein said spring is welded at one end to the flattened tip of said guidewire and at other end of said spring to the guidewire at the 8 thousandths of an inch diameter portion.

6. A device as described in claim 1 wherein said flexible coiled spring is welded to the guidewire at both ends of said spring.

7. A device as described in claim 1 wherein the distal end of said coiled spring extends approximately 2 centimeters beyond the distal end of the balloon of said PTCA catheter.

8. A device as described in claim 7 wherein the plastic sheath extends over said coiled spring from the proximal end of said spring to the distal end of said balloon.

9. A device as described in claim 1 wherein the internal diameter of said catheter body is greater than 20 thousandths of an inch; the outside diameter of said guidewire is between 14-16 thousandths of an inch; the tip of said guidewire tapers from 14-16 thousandths of an inch to a step of 8 thousandths of an inch and then to a tip of 3 thousandths of an inch in diameter; and said coiled spring has an internal diameter of 8 thousandths of an inch and outside diameter of 12 thousandths of an inch.

10. A device as described in claim 1 wherein said plastic sheath is secured about said guidewire by adhesive means and heat shrink means to form a dual sealed bond of plastic to wire.

11. A device as described in claim 10 wherein said plastic sheath is secured about the 8 thousandths step of the tip of said guidewire for a distance of approximately 2 millimeters.

12. A device as described in claim 11 wherein said thin walled balloon is secured at its proximal end to the distal end of said catheter body and at its distal end to said sheath for a length of approximately 5 millimeters.

13. A device as described in cl-aim 1 wherein said balloon is adhesively and thermally sealed to the distal end of said plastic sheath approximately 2 centimeters from the distal end of said coiled spring member.

14. A device as described in claim 1 wherein said control means comprises:

a dual lumen catheter body joined to the proximal end of said elongated catheter body with one lumen receiving the proximal end of said guidewire and the other lumen being in fluid communication with the interior of said catheter body;

said guidewire receiving lumen being interlocked with the proximal end of said guidewire whereby twisting of said dual lumen catheter body will cause the distal tip of said coiled spring to twist without twisting said balloon 15. The method of manufacturing a PTCA catheter that includes the steps of:

forming first and second reduced diameter sections adjacent each other in the distal end of a guidewire;

inserting said 1st and 2nd reduced sections into a coiled spring member;

welding said coiled spring to said guidewire at each end thereof;

enclosing said spring in a plastic sheath;

sealing said sheath about said guidewire at the proximal end of said spring;

inserting said guidewire into a catheter body having proximal and distal ends with said reduced diameter sections extending from the distal end of said catheter body;

forming a thin walled tubular balloon about the distal end of said catheter body and at least one of said reduced diameter sections of said spring and sheath covered guidewire;

sealing one end of said tubular balloon about the distal end of said catheter body;

sealing the other end of said tubular balloon to the sheath enclosing said spring at a point spaced from the distal end of said spring;

joining manipulating means to the proximal end of said catheter body; and securing the proximal end of said guidewire to said manipulating means.

* * * * *